(12) United States Patent
Dapprich (10) Patent No.: US 6,585,939 B1
(45) Date of Patent: Jul. 1, 2003

(54) MICROSTRUCTURES FOR USE IN BIOLOGICAL ASSAYS AND REACTIONS

(75) Inventor: Johannes Dapprich, Lawrenceville, NJ (US)

(73) Assignee: Orchid BioSciences, Inc., Princeton, NJ (US)

( * ) Notice: Subject to any disclaimer, the term of this patent is extended or adjusted under 35 U.S.C. 154(b) by 0 days.

(21) Appl. No.: 09/512,907

(22) Filed: Feb. 25, 2000

Related U.S. Application Data

(60) Provisional application No. 60/122,020, filed on Feb. 26, 1999.

(51) Int. Cl.[7] .................................................. B01L 3/00
(52) U.S. Cl. ..................... 422/99; 422/68.1; 422/82.05; 422/82.06; 422/100; 422/101; 435/283.1; 435/287.1; 435/287.8; 435/288.2; 435/288.3; 435/288.4; 436/174; 436/180; 264/239; 264/241; 264/250; 264/259; 264/297.1; 264/297.4
(58) Field of Search .......................... 422/55, 58, 68.1, 422/81, 82.05, 82.06, 99, 100, 129, 130, 131; 436/164, 174, 180; 435/283.1, 287.1, 287.8; 264/239, 240, 241, 250, 297.1, 297.4, 259, 299, 313

(56) References Cited

U.S. PATENT DOCUMENTS

| | | | | |
|---|---|---|---|---|
| 4,756,884 A | * | 7/1988 | Hillman et al. ............... 422/73 |
| 5,443,890 A | * | 8/1995 | Ohman ........................ 428/167 |
| 5,603,351 A | | 2/1997 | Cherukuri et al. |
| 5,637,469 A | * | 6/1997 | Wilding et al. ............. 435/7.21 |
| 5,645,702 A | * | 7/1997 | Witt et al. ................... 428/188 |
| 5,800,690 A | * | 9/1998 | Chow et al. ................. 204/451 |
| 5,842,787 A | | 12/1998 | Kopf-Sill et al. |
| 5,872,623 A | * | 2/1999 | Stabile et al. ................. 356/73 |
| 5,882,465 A | * | 3/1999 | McReynolds ............... 156/285 |
| 5,932,799 A | * | 8/1999 | Moles ........................ 73/53.01 |
| 5,957,579 A | | 9/1999 | Kopf-Sill et al. |
| 6,074,725 A | * | 6/2000 | Kennedy .................... 428/128 |
| 6,225,109 B1 | * | 5/2001 | Juncosa et al. .......... 435/288.5 |
| 6,268,219 B1 | * | 7/2001 | McBride et al. ............ 436/180 |

* cited by examiner

*Primary Examiner*—Jill Warden
*Assistant Examiner*—Dwayne K. Handy
(74) *Attorney, Agent, or Firm*—Kevin G. Mierzwa

(57) ABSTRACT

The present invention relates to microstructures which a fabricated from a cast or molded polymer material, such as polydimethylsiloxane (PDMS). The invention describes and claims methods and compositions from which a variety of microstructures may be prepared. The microstructures are particularly useful for use in assays and reactions in the relating to biological assays, including applications in medical diagnostics. Such assays and reactions included, but are by no means limited to, polynucleotide sequencing and polynucleotides analysis, including analysis of single nucleotide polymorphisms, and for polynucleotide amplification such as PCR.

The microstructures of the invention may contain many features that are useful for such applications. For example, the microstructures may comprise wells or channels for biological fluids and/or reagents, as well as pumps and valves for directing such fluids, e.g., in a biological assay. The microstructures may also comprise a variety of optical devices, including lenses, mirrors, optical waveguides, diffractions gratings, and optical absorbers and/or scatters such as "quantum dots."

38 Claims, 5 Drawing Sheets

(3 of 5 Drawing Sheet(s) Filed in Color)

MICROSTRUCTURES FOR USE IN BIOLOGICAL ASSAYS AND REACTIONS

RELATED APPLICATIONS

The present invention claims priority to U.S. provisional application Ser. No. 60/122,020, filed Feb. 26, 1999.

FIELD OF THE INVENTION

The present invention relates to methods and compositions for performing biological assays. Specifically, the invention provides compositions, referred to herein as microstructures, which may be used in micro-fabricated devices for a variety of biological applications, including nucleic acid sequence analysis and polynucleotide amplification, as well as other biological assays and reactions.

BACKGROUND OF THE INVENTION

Many techniques and assays have been developed for the analysis of biological samples. Practical applications of these techniques include the diagnosis of genetic diseases, the diagnosis of infectious diseases, forensic techniques, paternity determination, and genome mapping.

For example, in the field of nucleotide sequence analysis, many techniques have been developed to analyze nucleic acid sequences and detect the presence or absence of various genetic elements such as genetic mutations, and polymorphisms such as single nucleotide polymorphisms(hereinafter "SNPs"), base deletions, base insertions, and heterozygous as well as homozygous polymorphisms.

Currently, the most definitive method for analyzing nucleic acid sequences is to determine the complete nucleotide sequence of each nucleic acid segment of interest. Examples of how sequencing has been used to study mutations in human genes are included in the publications of Engelke et al. (1998, *Proc. Natl. Acad. Sci. U.S.A.* 85:544–548) and Wong et al. (1997, *Nature* 300:384–386). The most commonly used methods of nucleic acid sequencing include the dideoxy-mediated chain termination method, also known as the "Sanger Method" (Sanger, F. et al., 1975, *J. Molec. Biol.* 94:441; Porbe, J. et al., 1997, Science 238:336–340) and the chemical degradation or "Maxam-Gilbert" method (Maxam, A. M. et al., 1977, Proc. Natl. Acad. Sci. U.S.A. 74:560).

Restriction fragment length polymorphism (hereinafter "RFLP") mapping is another commonly used screen for DNA polymorphisms arising from DNA sequence variation. RFLP consists of digesting DNA with restriction endonucleases and analyzing the resulting fragments, as described by Botstein et al. (1980, Am. J. Hum. Genet. 32:314–331) and by White et al. (1998, Sci. Am. 258:40–48). Mutations that affect the sequence recognition of the endonuclease will alter enzymatic cleavage at that site, thereby altering the cleavage pattern of the DNA. DNA sequences are compared by looking for differences in restriction fragment lengths.

However, sequencing techniques such as the Sanger and Maxam-Gilbert methods involve series of nested reactions which are then analyzed on electrophoretic gels. RFLP analysis also requires analysis of reaction products on Southern Blots. These techniques can therefore be cumbersome to perform and analyze.

Alternative, simpler, and less cumbersome methods to analyze and/or sequence nucleic acid molecules have also been proposed. For example, there is considerable interest in developing methods of de novo sequencing using solid phase arrays (see, e.g., Chetverin, A. B. et al., 1994, Biotech. 12:1093–1099; Macevicz, U.S. Pat. No. 5,002,867; Beattie, W. G. et al., 1995, Molec. Biotech. 4:213–225; Drmanac, R. T., EP 797683; Church et al., U.S. Pat. No. 5,149,625; Gruber, L. S., EP 787183; each of which is incorporated herein by reference in its entirety) including universal sequencing arrays such as those described, e.g., by Head, S. et al. (U.S. patent application Ser. No. 08/976,427, filed Nov. 21, 1997, which is incorporated herein by reference in its entirety) and by Boyce-Jacino, M. et al. (U.S. patent application Ser. No. 09/097,791, filed Jun. 16, 1998, which is incorporated herein by reference in its entirety).

Other methods have been developed which use solid phase arrays to analyze single nucleotide polymorphisms (SNPs). For example, several primer-guided nucleotide incorporation procedures for assaying polymorphic sites in DNA have been described (e.g., Kornher, J. S. et al., 1989, Nucl. Acids Res. 17:7779–7784; Sokolov, B. P., 1990, Nucl. Acids Res. 18:3671; Syvanen, A.-C. Et al., 1990, Genomics 8:684–692; Kuppuswamy, M. N. et al., 1991, Proc. Natl. Acad. Sci. U.S.A. 88:11431147; Prezant, T. R. et al., 1992, Hum. Mutat. 1:159–164; Ugozzoli, L. et al., 1992, GATA 9:107–112; Nyren, P. et al., 1993, *Anal. Biochem.* 208:171–175; and Wallace WO89/10414).

An alternative "micro sequencing" method, the Genetic Bit Analysis (GBA''') method has been disclosed by Goelet, P. et al. (WO 92/15712). Several other micro sequencing methods have also been described, including variations of the $(GBA_{TM})$ 10 method of Goelet et al. (see, e.g., Mundy, U.S. Pat. No. 4,656, 127; Vary and Diamond, U.S. Pat. No. 4,851, 331; Cohen, D. et al., PCT Application No. WO 91/02087; Chee, M. et al., PCT Application No. WO 95/11995; Landegren, U. et al., 1998, Science 241:1077–1080; Nicerson, D. A. et al., 1990, Proc. Natl. Acad. Sci. U.S.A. 87:8923–8927; Pastinen, T. et al., 1997, Genome Res. 7:606–614; Pastinen, T. et al., 1996, Clin. Chem. 42:1391–1397; Jalanko, A. et al., 1992, Clin. Chem. 38:39–43; Shumaker, J. M. et al., PCT Application Wo 95/00669).

Other methods of nucleic acid analysis involve amplifying defined segments of nucleic acid sequence for subsequent analysis, e.g., by one or more of the micro sequencing methods discussed above. For example, the Polymerase Chain Reaction (PCR) is widely used to amplify defined segments of nucleic acid sequence in vitro. Generally, a targeted polynucleotide segment is flanked by two oligonucleotide primers. PCR consists of three steps that are repeated many times in a cyclical manner: (1) denaturing double-stranded polynucleotide sample at high temperature (about 94° C.); (2) annealing oligonucleotide primers to the polynucleotide template at low temperature (from about 37° C. to about 55° C.); and (3) extending primers using a template-dependent polymerase at a moderate temperature (about 72° C.).

PCR has been demonstrated in micro-fabricated devices consisting of a reaction chamber that has been etched into a silicon chip (see, e.g., Wilding et al., 1994, *Clin. Chem.* 40:1815–1818; Northrup et al., 1993, Transducers' 93:924–926), and continuous flow PCR has been accomplished on a chip (see, e.g., Kopp et al., 1998, Science 280:1046–1048). However, these devices have the major drawback of significant solution evaporation at the high temperatures used in PCR. Further, the devices do not contain integrated micro valves or micro pumps.

A powerful concept and method known as Microfluidic-senabled Target Amplification (MeTA), which may be used as an alternative to PCR, has been previously described as set forth in U.S. patent application Ser No. 08/924,763 (Kumar, R., "AMPLIFICATION METHOD FOR A POLYNUCLEOTIDE," filed Aug. 27, 1997) which is incorporated herein, by reference, in its entirety. This target amplification method is an isothermal process, using chemicals rather than high temperature DNA denaturation. MeTA method is preferably implemented using a micro-fabricated device such as the device disclosed in U.S. provisional application No. 60/110,367 (Fan, Z. H. et al., "MICROFLUIDICS-BASED DEVICE FOR DNA TARGET AMPLIFICATION" filed Nov. 30, 1998) which is incorporated herein, by reference, in its entirety.

However, implementation of such methods requires special micro-fabricated devices. Currently, such micro-fabricated devices are typically fabricated from glass, silicon, or plastic plates or slides, which may be etched with horizontal or vertical cells (chambers) and/or channels, e.g., by photolithography, chemical and/or laser etching, and bonding techniques. However, such devices are fragile and expensive to produce. Alternatively, techniques have been developed for fabricating surface relief patterns in the plane of self-assembled monolayers ("SAMs"). These techniques typically comprise casting a material such as polydimethylsiloxane (PDMS), in the form of a prepolymer, onto a complementary relief pattern (i.e., a "cast") and then curing the prepolymer (see, e.g., Wilbur et al., 1995, *Adv. Mater* 7:649652; Kumar et al., 1994, *Langmuir* 10:1498–1511; Xia Whitesides, 1995, *Adv. Mater* 7:471–473). The cured polymer is then used as an elastomeric stamp to form a pattern on the SAM.

However, there remains a need in the art for compositions which may be used in micro-fabricated devices for one or more bioassays such as those described above for polynucleotide analysis. In particular, such compositions should be easy to construct and relatively cheap and durable. Ideally, such compositions should also be constructed of a biocompatible material that has mechanical, optical, thermal, chemical, and electrical properties conducive to biological assays, and, in particular, to polynucleotide assays.

SUMMARY OF THE INVENTION

The present invention relates to polymer microstructures which may be used to construct or, alternatively, as part of micro-fabricated devices for biological assays. In particularly preferred embodiments the polymer microstructures of the invention are used in micro-fabricated-devices for polynucleotide analysis including, but by no means limited to, DNA micro arrays and Microfluidics devices, e.g., for PCR or MeTA polynucleotide amplification reactions.

The polymer microstructures of the invention include, but are by no means limited to, two-dimensional microstructures which may be sealed or bonded to a smooth surface such as glass. Alternatively, the two-dimensional microstructures of the present invention may also be sealed or bonded to the surfaces of other microstructures, including the surfaces of other two-dimensional polymer microstructures of this invention. Thus, the present invention also contemplates three-dimensional microstructures which may be formed by generating interlocking layers of microstructures.

The invention includes a variety of microstructures, and their use in a variety of applications for nucleotide sequence analysis, as well as for other biological applications. The microstructures of the invention include, for example, two dimensional arrays of channels and wells which may be used, e.g., to construct DNA micro arrays for polynucleotide sequence analysis. The microstructurs of the invention also include valves or pumps which comprise cavities (e.g., cells) in multilayered polymer microstructures and which may be used, e.g., to direct reagents in biological assays. The microstructures of the invention further include optical gratings, lenses, and reflective coatings, such as mirrors, which may be used, e.g., for signal detection or for sample illumination.

In preferred embodiments, the microstructures of the invention are fabricated from flexible polymer materials that include but are not limited to materials such as silicone, urethane, latex, or vinyl. The microstructures of the invention may also be fabricated from mixtures of such polymers and copolymers. In a particularly preferred embodiment, the microstructures of the invention are fabricated from polydimethylsiloxane (PDMS).

The invention is based, at least in part, on the discovery that microstructures generated by casting or molding and curing a polymer material such as PDMS onto a complementary relief pattern may be used for a variety of biological applications.

The microstructures of the present invention overcome the limitations of the prior art by providing microstructures that are durable and potentially re-usable, yet are cheap enough to be usable as disposable devices. The microstructures of the invention are also self-sealing, and able to form watertight seals on smooth surfaces by reversible bonds. Alternatively, the microstructures of the invention may be permanently bonded to another surface, e.g., by chemical treatment such as oxidative etching or use of an adhesive material. Thus, a microstructure of this invention can be readily attached, not only to surfaces such as glass or silicon, but also to the surface of another microstructure of the invention.

The microstructures of the present invention further improve upon the prior art in that they can be readily designed or modified to have particular properties which may be desirable for certain applications, e. g., in certain biological assays. For example, the surface of the microstructures may be coated or chemically modified with different chemicals or functional groups such as bovine serum albumin ("BSA"), glycine, polyethylene glycol ("PEG"), silanes, or other proteins or amino acid residues, to control surface properties, such as hydrophobicity, hydrophilicity, local surface pH, and chemical reactivity. The microstructures of the invention can also be designed to have particular bulk or regional mechanical and/or optical properties, e.g., by embedding or doping the microstructures with additional materials. For example, the microstructures of the invention can be embedded with fibers, particles and/or other polymers or copolymers to modify their mechanical properties. The microstructures of the invention may also be embedded with additives such as dyes or light absorbing or scattering particles, to modify their optical properties.

The microstructures of the invention are ideally suited for many biological applications, including assays which analyze and manipulate polynucleotide sequences. Such assays include, but are by no means limited to, assays for genetic analysis such as nucleotide sequencing assays and the detection and/or analysis of nucleotide polymorphisms such as base deletions, insertions, and SNPs. The microstructures are also well suited for in vitro biological reactions that may be performed in such assays. For example, the microstructures of the invention may be used to amplify polynucleotide sequences, e.g., by PCR or by MeTA amplification. Further, because the simple microstructures of the present invention may be combined to form more intricate, three dimensional microstructures, microstructures may also be designed and built which perform several biological reactions and/or assays simultaneously. For example, given what is taught herein, the skilled artisan may readily design and construct a microstructure which may be used, e.g., to perform sample extraction, amplify a polynucleotide sample (for example by PCR or by MeTA), and then detect SNPs in that sample on a micro array.

Biological assays and/or reactions using the microstructures of the invention require only small amounts of sample, and may be readily automated. Signal detection and analysis are also facilitated in assays using the microstructures of the invention since the optical properties of the microstructures can be adjusted to incorporate features such as optical wave guides, diffraction gratings, lenses and mirrors.

Thus, biological samples may be optically excited and signals may be directly detected within or through the microstructures, e.g., by means of an integrated device, for instance using diode lasers, total internal reflection MR), or surface plasmon resonance (SPR), CCD or other detectors, including sample imaging, for instances by lenses or lens arrays or through proximity focused detection. Alternatively, the microstructures of the invention may be readily removed, e.g., from a silicon or glass plate or slide, to expose a sample for signal detection and/or for subsequent use or analysis (e.g., in another biological assay).

The microstructures of the present invention are simple, robust, and inexpensive to produce, and may be readily customized for use in a variety of applications. Indeed, the microstructures are ideally suited for automated biological assays and robotic handling of fluids or of the microstructures, including assays for polynucleotide sequence analysis.

BRIEF DESCRIPTION OF THE DRAWINGS

The file of this patent contains at least one drawing executed in color. Copies of this patent with color drawings will be provided by the Patent and Trademark Office upon request and payment of necessary fee.

DETAILED DESCRIPTION OF THE INVENTION

In the following figures the same reference numerals are used to identify the same components.

The present invention includes compositions, hereinafter referred to as microstructures. These compositions may be used for biological applications, and, in particularly preferred embodiments, are used-for assays that involve the analysis of polynucleotide molecules. Such assays include, for example, genetic analysis such as DNA sequencing and/or analysis of genetic polymorphisms, including single nucleotide polymorphisms (SNPs). The microstructures of the invention may also be used for other reactions and/or assays that involve biological materials, including, but by no means limited to, antibody and/or protein assays, as well as assays that involve manipulation of living cells.

Figure 1A:
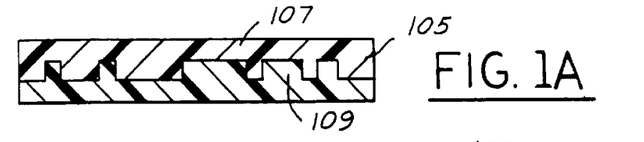
FIG. 1A is a cross-sectional view of a layer of PDMS material being cast on a single relief pattern.
Figure 1B:
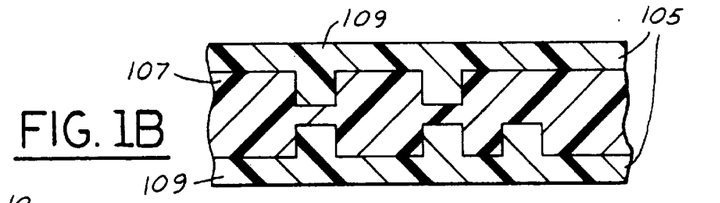
FIG. 1B is a cross-sectional view of a layer of PDMS material being cast on a double relief pattern.

Referring now to FIGS. 1A and 1B, the invention is based, at least in part, on the discovery that microstructures generated by casting and curing a polymer material 107 such as PDMS onto a complementary relief pattern 109 of a mold 105, or by molding and curing a polymer material such as PDMS between two juxtaposed relief patterns 109 of a mold 105 may be used for a variety of biological applications.

The microstructures of the invention are simple and inexpensive to produce, and may be readily customized for a wide variety of applications. In particular, the microstructures are ideal for automated, biological assays, including assays for polynucleotide sequence analysis.

The following subsections present the compositions of the invention in greater detail. In particular, Section 1 first describes microstructures which are casted from and may be attached to a flat surface, as well as methods for producing such microstructures. Section 1 also describes microstructures which are molded by sandwiching the polymer material between two juxtaposed relief surfaces, as well as methods for producing such microstructures. Section 2 describes generally how more intricate, three-dimensional structures may be produced by layering the individual microstructures described in Section 1. Finally, Sections 3 and 4 describe particular types and/or components of microstructures which may be generated according to the methods described in Sections 1 and 2. In particular, Section 3 describes various microfluidic components such as microfluidic chambers, and microfluidic valves and pumps. Various optical devices, including, input couplers, reflective coatings, lenses, are described in Section 4. optical-filters, such as dyes, optical scatters, and optical absorbers, which may be incorporated into the microstructures of the invention, are also described in Section 4.

The descriptions are by way of exemplary illustrations of the general methods and compositions of the invention. These examples are non-limiting, and related variants that will be apparent to one of skill in the art are intended to be encompassed by the appended claims. In particular, in certain particularly preferred embodiments the microstructures of the invention are fabricated from polydimethylsiloxane (PDMS). However, as is readily appreciated by one skilled in the art, the microstructures of this invention may also be fabricated from other materials, including, but by no means limited to, latex, silicone, urethane, and vinyl. Accordingly, although the below description may refer, in particular, to microstructures fabricated from PDMS, it will be understood by the skilled artisan that such disclosure is applicable to microstructures fabricated from other materials as well, including the materials recited above.

Section 1. Microstructures on Flat Surfaces

Referring now to FIGS. 1A and 1B, microstructures which may be used, e. g., in biological assays can be readily made from a polymer material such as PDMS by casting the material, in the form of a prepolymer, onto a complementary relief pattern (i.e., a "cast"). PDMS structures with simple relief patterns have also been used, e.g., to immobilize immunoglobulins on a solid surface in specific two-dimensional patterns (Delamarche et al., 1997 Science 276:779–781), and to form reaction containers for DNA-bead attachment for a single molecule DNA sequencing reaction (Dapprich & Nicklaus, 1998, Bioimaging 6(1): 25–32). Methods for casting relief patterns on the surface of PDMS are well known in the art for the formation of elastomeric stamps (see, e.g., Wilbur et al., 1995, *Adv. Mater* 7:649–652; Kumar et al., 1994, *Langmuir* 10:1498–1511; Xia & Whitesides, 1995, *Adv. Mater* 7:471–473), wherein the resulting stamps are subsequently used to form patterns in the plane of self-assembled monolayers (SAMs). However, the present invention is based, at least in part, on the discovery that such cast polymers may themselves be used as microstructures for various applications.

Casts of intermediate resolution and depth (several hundred micrometers) for PDMS or other polymer materials can be quickly and easily made, e.g., by routine photolithography techniques well known to those skilled in the art. For example, such casts can routinely be made using photoresistcovered flat substrates. One or more layers of sheet photoresist, such as Morton chemical dynachem 3 mil=75 microns thick negative photoresist, may be laminated onto a smooth glass surface or some other smooth substrate. Multiple layers of the photoresist may be laminated onto the smooth substrate to achieve a particular desired thickness. Relief contours, e.g., for channels and/or wells in a flat PDMS microstructure, can then be etched into the photoresist. Sub-millimeter resolution is possible for this process using double transparencies as a mask, wherein the relief pattern is primed on the transparencies e.g., on a black-and-white laser printer by means of a conventional drawing program. The relief pattern may also be reproduced from a printed relief pattern using a photo copier.

Other resist materials are also available and well known to those skilled in the art, and such other materials may also be used to prepare casts for the microstructures of the present invention. One skilled in the relevant art(s) will readily appreciate which particular resist materials are preferable for particular embodiments of the invention. For example, SU-8 (available from International Business Machines, Corp.) is a resist which is preferable for fabricating casts having a large thickness and high aspect ratio. Sub-micrometer accuracy casting is possible on such resists with conventional lithographic techniques using flat substrates. Such lithographic techniques are well known to those skilled in the relevant art(s). Flat substrates which may be used in such lithographic techniques include, for example, glass, silicon, and polished metal, including copper, brass, and aluminum.

Microstructures which may be used, e.g., in biological assays-can also be readily made from a polymer material such as PDMS by molding the material, in the form of a prepolymer, by sandwiching it between two juxtaposed relief patterns (i.e., a "mold"). Molds can be made in two pieces using the same materials and processes as described above for casts. The two pieces are then used to sandwich a prepolymer, and the resulting microstructure will have relief patterns on two sides. Molds can also be made in one piece, e.g., by carving out a pattern from one solid piece of material. These relief patterns need not necessarily be identical or connected, but may be in order to be adapted to a particular application or device.

As noted above, the microstructures of the present invention are most preferably composed of PDMS. However, the invention also encompasses microstructures composed of other materials on which sub-millimeter surface features may be formed by casting the material on a complementary relief pattern or molding the material by sandwiching it between two juxtaposed complementary relief patterns. For example, the invention also encompasses microstructures fabricated from latex, urethane, vinyl and silicone, as well as other natural and synthetic polymers (see, e.g., U.S. Pat. No. 5,807,921 to Hill et al.). The invention also encompasses microstructures composed of polymers containing other additives. For example, silica particles or other polymers may be embedded into the material to modify the mechanical properties of a microstructure such as stiffness and/or hardness. Such additives include, for example, any of numerous commercial formulations which exist, and are well known in the art, for use in other applications such as medicine, electronics, meteorology, and quality control. Such additives also include dyes, absorbing or scattering particles, or quantum dots which may be embedded into the material to modify the optical (e.g., light absorbing or scattering) properties of the microstructure.

Surface modifications of PDMS are well known to those skilled in the art (see, e.g., moue et al., 1990, J. Appl. Pol. Sci. 41:1815–1829; Koberstein, 1996, Mrs. Bulletin; Andrade & Chen, 1986, Surf. and Interface Anal. 8:253–256; Van Alstine et al., 1993, Colloids and Surfaces A: Physiochemical and Engineering Aspects 77:149–158; U.S. Pat. No. 5,777,026 to Berg et al.).

Preferably, the material is one which is capable of forming a reversible bond or seal with a smooth surface, such as a glass or silicon surface. More preferably the material is self-sealing such that a microstructure of the invention is capable of forming a reversible bond or seal with another microstructure of the invention.

Figures 1C, 1D, 2, 3:
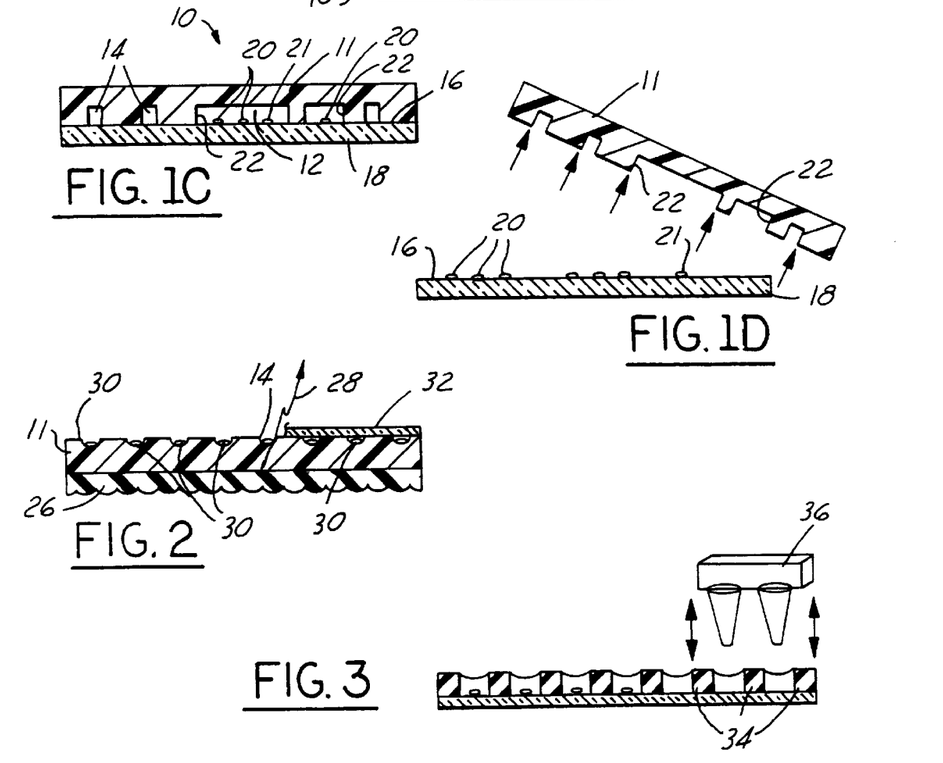
FIG. 1C is a schematic illustration of a microstructure made from a single cast layer of PDMS; the microstructure contains channels and reservoir for isolating samples, and is reversibly bound to a substrate such as a glass plate.
FIG. 1D illustrates schematically how the microstructure may be optionally removed from the glass plate to expose the samples attached thereto.
FIG. 2 is a schematic illustration of a microstructure made from a single cast layer of PDMS and containing several wells in which a biological same is placed or attached; the PDMS layer is optionally covered, e.g., with a glass plate and may be placed directly on a detector for signal detection through the PDMS.
FIG. 3 is a schematic illustration of an "open" microstructure comprising spacers or delimiters formed from PDms attached to a flat substrate, and acting as seals between two flat substrates.

Referring now to FIGS. 1C and 1D, such microstructure assemblies 10 may therefore include microstructures 11 containing cells 12 or channels 14 which are cast from a relief contour as described above, and placed on a smooth surface 16 of a substrate 18, such as a glass surface, as illustrated, for example, in FIG. 1. Such microstructures may also include microstructures containing cells 12 or channels 14 which are molded from two juxtaposed relief contours as described above. In certain embodiments, one or more biological samples 20 (such as one or more polynucleotide samples), or reagents 21 (such as an antibody or polynucleotide probes or primers), are attached to the flat surface. The walls 22 between the self-sealing cells 12 and/or channels 14 in the microstructure 11 may then function to isolate each sample and/or reagent, and prevent cross contamination. Other samples, reagents, and/or solutions necessary for the assay may be delivered to each sample, for example, through channels in the microstructure. As is best shown in FIG. 1(b), in preferred embodiments wherein the seal between the microstructure 11 and the surface 16 is reversible, the microstructure can be readily, removed, e.g., at the completion of the assay, to access the samples) or reagent(s). For example, in certain embodiments, the microstructure 11 may be removed upon completion of a particular assay and a signal detected on the glass slide.

Referring now to FIG. 2, in other alternative embodiments, the microstructure may be either permanently or temporarily attached or fixed directly to a detector 26, such as a CCD chip, a diode array, or a photocathode, and a signal 28 may be detected through the microstructure 11, as illustrated, for example, in FIG. 2. In such embodiments, samples 20 and/or reagents 21 may be attached directly to a flat surface to which the microstructure 11 is subsequently attached. Alternatively, however, the samples and/or reagents may be in wells 30 or channels of the microstructures, as illustrated in FIG. 2. In such embodiments, the microstructure 11 is preferably sealed with a cover layer 32 which may be, e.g., a glass cover slip or a thin film or layer of material such as PDMS or other polymer.

Referring now to FIG. 3, "open" microstructures 11 are also anticipated which comprise spacers 34 or delimiters on substrate 18 that define wells 30. Direct access into the wells 30 is possible, e.g., by means of conventional vertical pipetting or dispensing devices 36 such as mechanical transfer (for particles of prepackaged reaction mixtures, syringe action, pin transfer, piezo dropper, electrospray, and other methods which will be apparent to those skilled in the art).

Figure 4:
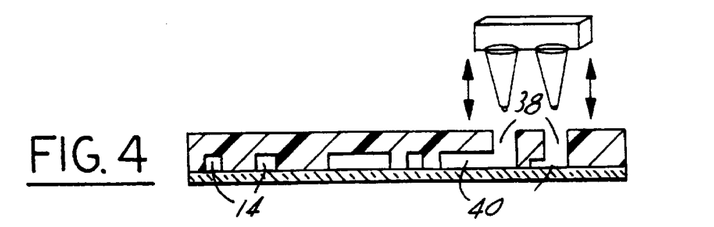
FIG. 4 is a schematic illustration of a microstructure made from a single cast layer of PDMS attached to a flat substrate.

Referring now to FIG. 4, microstructures 11 that contain combinations of all of the above-described structures are also anticipated. As illustrated, an exemplary microstructure which comprises an array of "open" sample inlet ports 38 and sample-preparation or pre-reaction wells 40 that are connected to a "covered" network of channels for sample processing, hybridization, or reaction.

Such microstructures may be readily produced in large sheets that are subsequently cut into pieces to fit a particular device or application. The microstructures are inexpensive, may be readily mass produced, are sterile, and biocompatible. Such structures are durable enough that they may readily be re-used several times, but are sufficiently inexpensive and mass producible so that they may also be used as disposable apparatuses. Routine techniques that are well known in the art may be used to manipulate and/or maintain a certain surface energy of a polymer such as PDMS. Thus, the microstructures of the invention can also be coated or modified, e.g., to form microtextured surfaces that are hydrophilic inside sample vessels (i.e., inside channels and/or cells) and hydrophic elsewhere to assist and control correct placement of sample and to control fluid flow (see, e.g., Columbus, 1987, Clin. Chem. 33(9) :1531–1537). Samples or reagents may also be attached or "printed" onto a microstructure, e.g., by applying an electrical charge across the microstructure to take up and release charged molecules.

Figure 5:
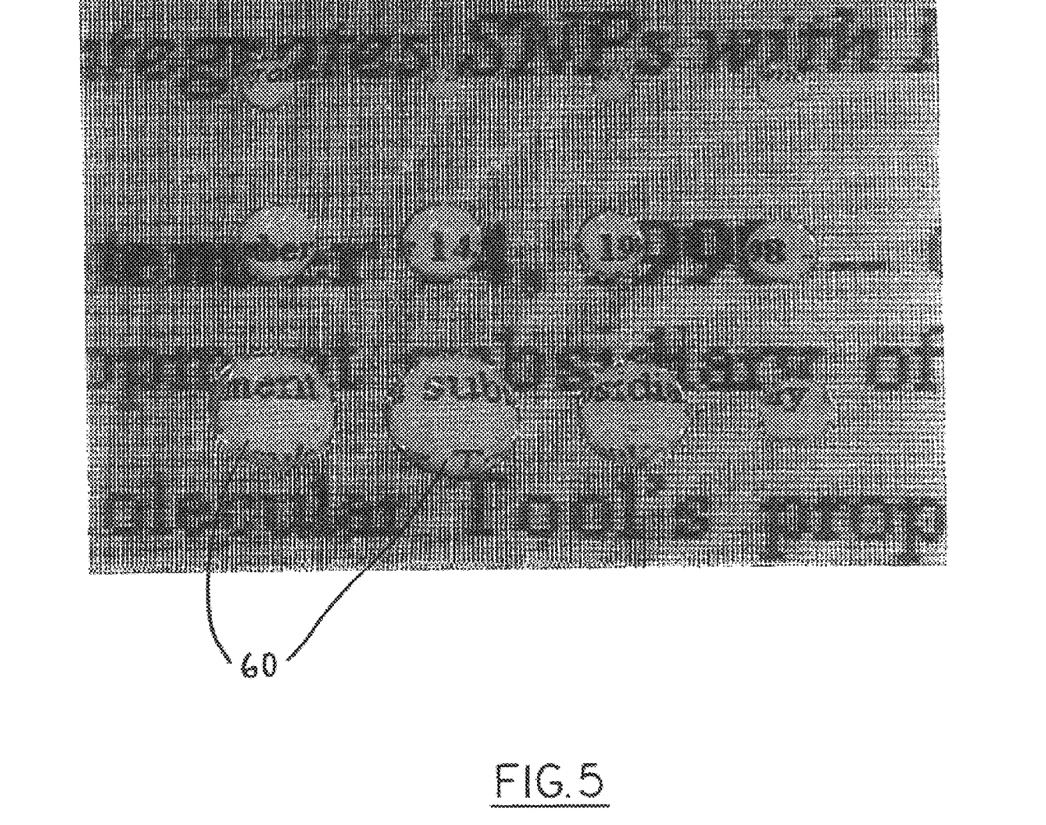
FIG. 5 is a photograph of a cast layer of PDMS which contains a plurality of chambers (dark) and is attached to a glass plate.
Figure 6:
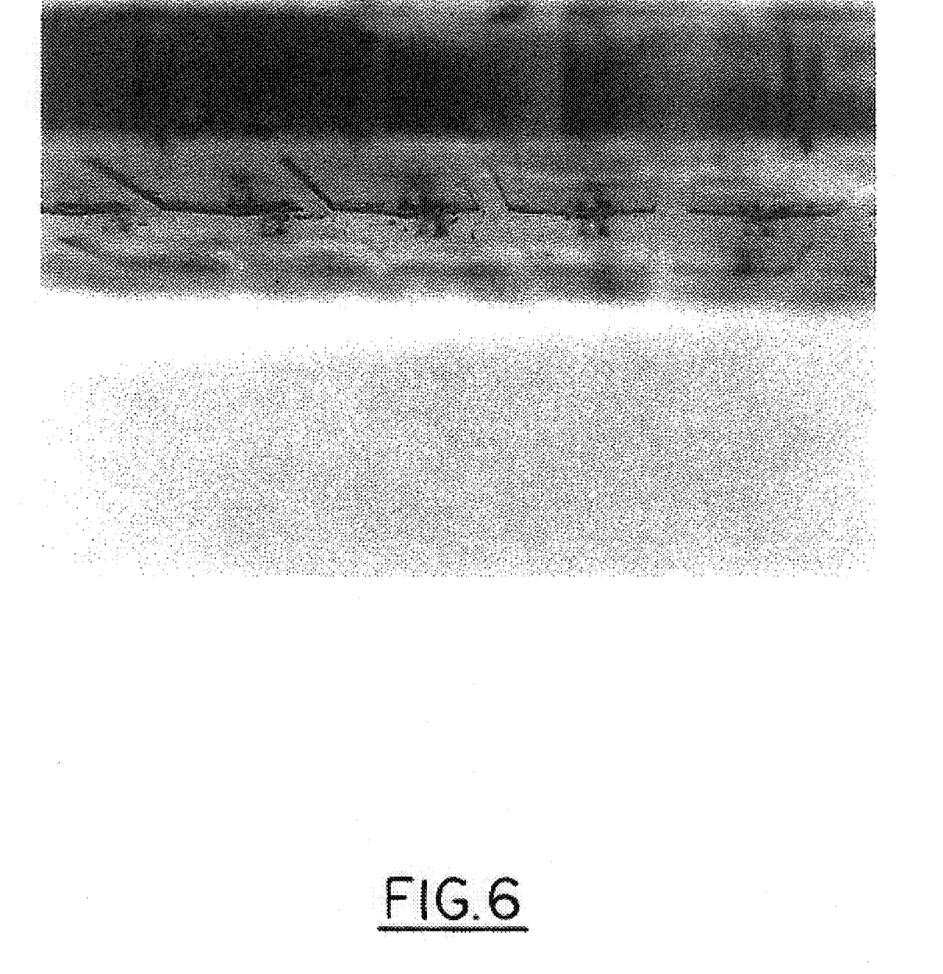
FIG. 6 is a profile view of the PDMS layer shown in FIG. 5.

Referring now to FIG. 5, an exemplary single layer PDMS microstructure. Specifically, the figure provides a photograph of a cast PDMS layer which has been applied onto a glass plate, and has a plurality of channels. Each of the channels has been filled with a colored liquid via holes (dark circle) that were punched through the PDMS at either end of each channel. A profile view of the same layer of PDMS is shown in FIG. 6. Here the PDMS layer has been turned over so that the channel side is face up, and the glass plate has been removed.

Section 2. Multilayered and Hybrid Material Structures

Figure 7:
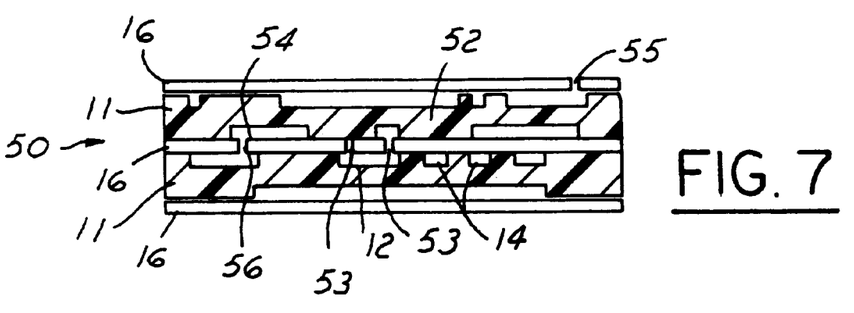
FIG. 7 is a schematic illustration of a hybrid microstructure comprising cast layers of PDMS and glass plates.

Referring now to FIG. 4, in addition to microstructures which are cast or molded onto a single layer of polymer, such as the structures described in Section 1 above, the present invention also encompasses more intricate, three-dimensional microsiructures. Specifically, the microstructures of the invention also include composite microstructure assemblies 50 which may be formed from two or more single-layer microstructures. Such structures may be composed entirely of single-layer microstructures of PDMS (o r of some other moldable polymer) or, alternatively, may be hybrids between, for example, single-layer PDMS microstructures 11 and a substrate having flat smooth surfaces such as glass, silicon, metal, or some other material. An example of such a microstructure is shown schematically in. FIG. 7.

A single layer of a polymer such as PDMS may be readily structured on both sides during molding according to the methods described in Section 1 above. In preferred embodiments wherein the single-layer microstructures are composed of a polymer, such as PDMS, which is self-sealing, more intricate microstructures can be formed by attaching interlocking pieces or layers of these single-layer microstructures. Such pieces could then be held together by their own surface adhesion.

Alternatively, individual single-layer microstructures can be fused together by means of an adhesive, such as a thin layer of polymer. For example, two surfaces may be coated with a thin layer of premixed but uncured PDMS which is then cured to form a PDMS "glue." Such a layer of PDMS may be applied, e.g., by spin coating PDMS onto a thin surface, and then contacting the thin surface with a microstructure so that only the surface of the microstructure which will contact another microstructure surface, e.g., in a layer, is coated. The coating of any recessed features in the microstructure, such as wells and channels, is thereby prevented.

Connections 52 may be readily constructed, e.g., between channels 14 and/or cells 12 in adjacent layers of microstructure 11. Connection 52 such as holes may be simply punched through the polymer material (e.g., through PDMS), or other, art recognized means of drilling through polymers such as PDMS, or through other materials, in the case of hybrid structures, may be employed. For example, excimer drilling produces high aspect ratio (<10) holes through PDMS. Connections 53 may also be found through a substrate or substrates as desired. For example, a sample inlet port 55 may be formed in a top substrate layer 16.

Connections 52 may form fluid interconnections between the different layers of pieces of a microstructure. Holes in the bottom of a sample containing vessel 54 or cell 12 in a microstructure can also form a capillary break 56. Thus, an underlying structure may be kept unexposed unless and until fluid is forced downwards by means of a controlled, applied pressure from above.

Connections 52 such as holes in a microstructure may also be constructed according to the above methods, e.g., to provide a macro-microinterface between an inlet or outlet port of a microstructure and a bigger orifice, e.g., for some collecting device. In addition, a gel or absorbent matrix layer may be disposed at the outlet of a microstructure in order to perform diagnostic tests, such as electrophoresis, Southern blotting, Western blotting, and the like, or amplification, for example PCR, on the contents of the microstructure. If the interfacing layer is made of a moldable polymer such as PDMS, the macro-microinterface can be achieved by contacting the inlet or outlet ports of the microstructure to another orifice, e.g., of a collection device, by slightly pressing the connecting orifice onto the holes in the polymer. The connecting orifice is preferably bigger in diameter than the hole in the PDMS, and rests on top of rather than being inserted into the PDMS. The force required to make a reliable seal is small enough that the process may be readily parallelized, e.g., for automated introduction and washing steps. It is also possible to remove liquid from a microstructure through such a macromicrointerface by simple aspiration, i.e., by suction of a connected device such as a syringe with a larger diameter than the outlet hole in the PDMS. Such a technique is particularly useful in many assays, e.g., when working with samples that cannot be allowed to mix with other fluids present in the microstructure.

Section 3. Microfluidic Devices and Structures

The microstructures of the present invention can be assembled to comprise many functional components which may be used, e.g., for practicing a variety of reactions and assays. For example, cavities in a multi-layered microstructure (e.g., a mufti-layered PDMS microstructure) or cavities in a single-layered microstructure (e.g., a single-layered PDMS microstructure) can function as valves or pumps to direct fluids containing samples, reagents, or solvents to particular locations in a microstructure (such as to a particular reaction chamber) during a reaction or assay. In particular, fluids can be displaced and forced through a channel of a microstructure by increasing or decreasing the pressure on a chamber connected to the channel.

In one embodiment, the pressure in a chamber connected to a chamber may be increased or decreased mechanically; i.e., by mechanically pressing down on the chamber to compress and thereby increase the pressure and by mechanically pulling up on the chamber to expand and thereby decrease the pressure. Such mechanical compression and/or expansion of a chamber could readily be achieved, e.g., by means of a mechanical pump or other device (see, e.g., U.S. Pat. No. 5,788,468 to Dewa et al.; U.S. Pat. No. 5,846,396 to Zanzucchi et al.).

In other, embodiments, the pressure in the chamber is increased or decreased by other means, such as by thermal expansion (or contraction) (see, e.g., Burns et al., 1996, Proc. Natl. Acad. Sci. USA 93:5556–5561), evaporation (or condensation), or modification of surface tension. In such embodiments, the increase or decrease in pressure in the chamber is most preferably realized by optical means, e.g., by means of a directed beam that causes a change in the "pump state" (i.e., the increased or decreased pressure state of the chamber).

Thus, samples and reagents may be readily directed through a microstructure, e.g., through sets of connected reservoirs, for different stages of a reaction or assay. Alternatively, fluids may be cycled through a microstructure or through zones of a microstructure, e.g., to increase hybridization or reaction efficiency. Indeed, as will be readily appreciated by the skilled artisan, microstructures capable of numerous dynamic and variable fluidic structures may be readily designed and constructed for a variety of applications, and without any undue experimentation.

Extended, linear cavities or channels in a microstructure of the present invention can also be used as pumps. Such structures are particularly useful for pumping fluids in a continuous fashion. Continues pumping through linear cavities or channels in a microstructure may be accomplished by means of a rolling or tilting device to progressively squeeze an extended channel or cavity, and force its contents in a particular direction. Such techniques are well known in the art, and are routinely used, e.g., in peristaltic pumps.

Such pumps are particularly useful in microstructures which are used for an application (e.g., an assay or reaction) which has a small sample transport volume and requires high accuracy of the dispersed or aspirated volume and also requires comparatively high pressures. For example, such pumps may be used to transfer samples fromone compartment of a microstructure into wells or into an absorbent matrix or gel for subsequent analysis or reactions. Such pumps may also be used to perform a washing step during a particular reaction or assay.

Fluid flow through a particular channel may readily be regulated by means of such pumps. In particular, a fluid may be pumped through such a channel at the appropriate time during an assay or reaction, by then applying the requisite pressure to the channel. At other times, when fluid should not be pumped through the channel, the opening (preferably in combination with the hydrophobic surface interactions of the polymer from which the microstructure is constructed) functions as a capillary break blocking release or transport of fluid.

Section 4. Optical Devices and Structures

The microstructures of the present invention may also comprise one or more optical components, including refractive and reflective components such as lenses and mirrors, and diffractive components such as input-coupler gratings, fresnel lenses, and holographic components.

Polymer materials such as PDMS, from which the microstructures of the invention are preferably constructed, can be cast or molded, using techniques well known in the art, into shapes that act as lenses, or can be cast or molded and coated with a thin reflecting surface to act as mirrors. For example, miniature lenses (i.e., millimeter or submillimeter size) with negative focal lengths and concave mirror shapes can be cast or molded from materials such as, for example, epoxy resin, which are spotted and cured on a flat substrate. Alternatively, the polarity of such a cast or mold can also be inverted, e.g., by using a different resin or a different casting or molding technique, to obtain lenses having positive focal lengths and convex mirror shapes. Such reflective and refractive structures may be cast or molded directly to a microstructure or, alternatively, they may be cast or molded separately and attached to another microstructure as described in Section 2 above.

Figure 8:
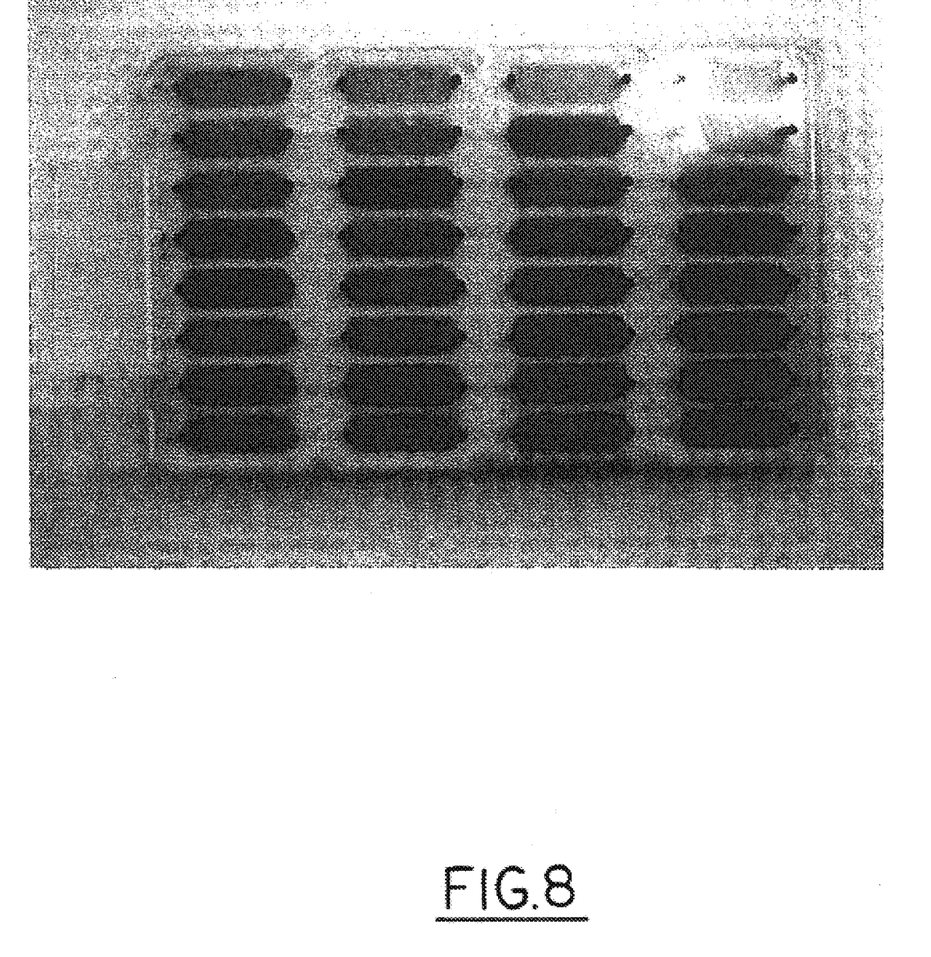
FIG. 8 shows lenses molded out of PDMS and attached to a computer screen to demonstrate their refractive properties.

Referring now to FIG. 8, several lenses 60 cast out of PDMS are shown. The lenses are attached to a computer screen to illustrate their refractive properties.

Figure 9:
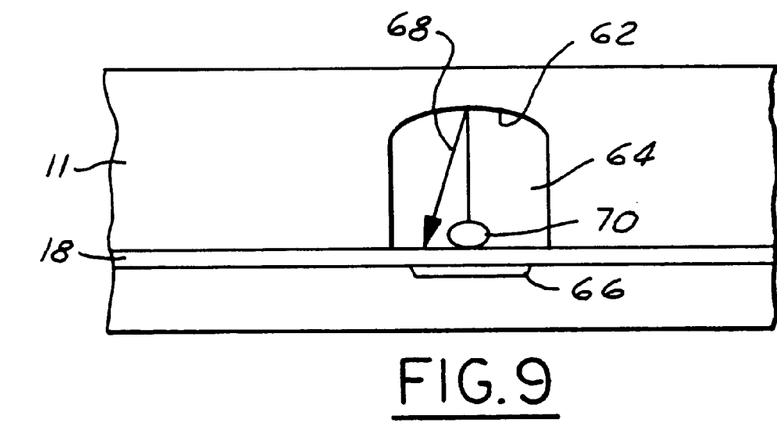
FIG. 9 is a cross-sectional view of a mirror and detector assembly formed of PDMS.

Referring now to FIG. 9, such lenses and mirrors can be used in microstructures of the invention, e.g., for optical signal detection. For example, if a PDMS sheet or microstructure 11 having a concave reflective surface 62 is placed on the side of a sample holder 64 that is opposite a detector 66, the light collection efficiency from the sample can be nearly doubled. In particular, light 68 from the sample 70 which is emitted away from the detector will be focused by the PDMS mirror back through the sample and onto the detector. Such a design is particularly well suited for microstructures which are intended to hold luminescent samples that do not require external excitation.

In other embodiments, different geometries of lenses and/or mirrors may be used to redirect excitation or emission light according to the needs of a particular application. For instance, focusing lenses or lens arrays made from PDMS and incorporated into the microstructures of the invention can relay light over a separating distance between a detector and a sample. Such lenses can also be arrayed to match particular sample distribution patterns or particular reaction wells in a microstructure, e.g., to magnify a region of the microstructure containing, for example, a sample having a visible signal for imaging, e.g., with a PC scanner.

Diffractive optical components, for example input coupler gratings, may also be fabricated out of PDMS or a polymer with similar properties by the casting or molding techniques described above. Such devices may be cast or molded directly on a microstructure or, alternatively, may be cast or molded separately and attached to another microstructure as described in Section 2 above. Other diffractive elements, such as fresnel lenses or holographic components may likewise be fabricated and incorporated into the microstructures of the invention. Diffractive optical components such as these are useful, e.g., for sample illumination or readout such as total internal reflection and evanescent wave excitation.

The optical features which may be included in the microstructures of the present invention further include optical filters such as dyes, optical absorbers, optical scatterers, and quantum dots which may be incorporated into the microstructure of the present invention. Such additives can be embedded into PDMS or other polymer materials to modify the optical properties either in bulk or in discrete parts or regions. Thus, layers or regions can be created within a microstructure that are selective for transmission or absorption of light at certain wavelengths. Such regions could be used, for example, to suppress excitation light scattering and internal fluorescence, including PDMS autofluorescence, while permitting a desired signal (e.g., sample fluorescence) to penetrate a microstructure to a detector.

Waveguides and/or light guides may also be included in the microstructures of the present invention, e.g., for localized excitation of samples within a microstructure at specific wavelengths. Such light guides may be constructed, e.g., by combining the above-described optical filtering components with reflective (e.g., metallized) layers and/or structures. Further, multilayered structures, such as those described in Section 2 above, can also be used to introduce light guides into a microstructure by using layers of different compositions which have different indices of refraction. Such structures would be preferably cast or molded and assembled in separate successive steps as explained in Section 2 above, and would include one or more steps of preparing layers having patterned metallic coatings or light guides, which become embedded in the final microstructure.

All references cited herein are incorporated herein by reference in their entirety and for all purposes to the same extent as if each individual publication or patent or patent application was specifically and individually indicated to bed incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A microstructure comprising:
   a first rigid flat substrate having a first surface and a second surface;
   a first flexible layer coupled to said first surface, said first flexible layer having a first plurality of one or more cells or channels;
   a second flexible layer coupled to said second surface of the first rigid flat substrate to form the composite microstructure, said second flexible layer having a second plurality of one or more cells or channels.

2. The microstructure of claim 1, wherein said first rigid flat substrate comprises a layer of glass, silicon, or metal.

3. The microstructure of claim 1, wherein said first flexible layer and said second flexible layer is fabricated from polymethylsiloxane.

4. The microstructure of claim 1, wherein the first and second flexible layers are attached by means of an adhesive layer.

5. The microstructure of claim 1, wherein the first and second flexible layers are self-sealing against the first and second surface.

6. The microstructure of claim 1, said microstructure further comprising a linear cavity or channel, and means for progressively squeezing the linear cavity or channel.

7. The microstructure of claim 1, further comprising fluidic connections between said first plurality of one or more cells or channels and said second plurality of one or more channels.

8. The microstructure of claim 7, wherein the connections comprise holes through the rigid flat layer for fluidically coupling said first flexible layer and said second flexible layer.

9. The microstructure of claim 8, wherein one of said holes and one of said first plurality of one or more cells or channels form a capillary break.

10. The microstructure of claim 7, said microstructure further comprising a cavity and a channel, further comprising means for displacing fluid through the channel by increasing or decreasing a pressure in the cavity.

11. The microstructure of claim 10, wherein the means for displacing comprise a means for increasing or decreasing the pressure in the chamber by mechanically contracting or expanding the cavity.

12. The microstructure of claim 10, wherein the means for displacing comprises means for increasing or decreasing tie pressure in the chamber by optical means.

13. The microstructure of claim 1, wherein the microstructure further comprises a lens or mirror molded from a flexible polymer layer.

14. The microstructure of claim 13, wherein the lens or mirror is molded directly to the microstructure.

15. The microstructure of claim 13, wherein the lens or mirror is molded separately and attached to the microstructure.

16. The microstructure of claim 13, wherein the lens or mirror is used in an optical signal detection means.

17. The microstructure of claim 13, wherein the lens or mirror redirects excitation or emission light.

18. The microstructure of claim 1, further comprising a diffractive optical component.

19. The microstructure of claim 18, wherein the diffractive optical component is molded from a flexible polymer layer.

20. The microstructure of claim 19, wherein the diffractive optical component is molded directly to the microstructure.

21. The microstructure of claim 18, wherein the diffractive optical component is molded separately and attached to the microstructure.

22. The microstructure of claim 18, wherein the diffractive optical component is one selected from the group consisting of an input coupler grating, a fresnel lens and holographic component.

23. The microstructure of claim 1, wherein the microstructure further comprises an optical filter.

24. The microstructure of claim 23, wherein the optical filter is one selected from the group of a dye, an optical absorber and an optical scatterer.

25. The micro structure of claim 23, wherein the optical filter is embedded into the flexible polymer layer.

26. The microstructure of claim 23, further comprising one or more reflective layers or structures, wherein said reflective layers or structures and said optical filter form a waveguide.

27. A microfluidic microstructure comprising a flexible polymer layer, wherein the flexible polymer layer is formed by casting a flexible polymer onto a complementary relief pattern by sandwiching the flexible polymer layer between two juxtaposed complementary relief patterns of a mold to form one or more cells or channels in a first surface and a second surface of the flexible polymer layer and attaching the first surface and the second surface of the flexible polymer layer to a respective first rigid flat surface and a second rigid flat surface so that said flexible polymer layer is positioned therebetween.

28. The microstructure of claim 27, wherein the flexible polymer layer is fabricated from polymethylsiloxane, silicone, urethane, latex, or vinyl.

29. The microstructure of claim 27, wherein one or more biological samples are attached to said first surface, such that the biological samples are positioned in said one or more cells or channels.

30. The microstructure of claim 27, said microstructure being attached to the surface by means of a reversible seal.

31. The microstructure of claim 27, wherein one or more biological samples are positioned on one or more cells or channels on a first surface of the flexible polymer layer, and a second surface of the flexible polymer layer is positioned on a detector, such that the one or more biological samples are detected through the flexible polymer layer.

32. The microstructure of claim 27, further comprising a plurality of wells, wherein the flexible polymer layer forms spacers between said wells.

33. The microstructure of claim 27, further comprising an array of wells, said wells being connected to a network of channels.

34. The microstructure of claim 27, wherein said flexible polymer layer has a fluidic connection therethrough.

35. A method of forming a microfluidic microstructure assembly comprising the step of:

forming a first flexible polymer layer between two juxtaposed complementary relief patterns of a mold to form one or more cells or channels in a first surface and a second surface of the first flexible polymer layer;

forming a second flexible polymer layer between two juxtaposed complementary relief patterns of a mold to form one or more cells or channels in a first surface and a second surface of the second flexible polymer layer; and attaching the first surface of the first flexible polymer layer and the first surface of the second flexible polymer layer to a respective first rigid flat surface and a second rigid flat surface of a first substrate.

36. The method of claim 35 wherein said step of attaching comprises removably attaching the first surface of the first flexible polymer layer and the first surface of the second flexible polymer layer to a respective first rigid flat surface and a second rigid flat surface of the substrate.

37. The method of claim 35 further comprising coupling a second substrate to the second surface of the first substrate.

38. The method of claim 35 further comprising coupling a second substrate to the second surface of a third substrate.

* * * * *